United States Patent [19]
Murphy et al.

[11] 4,414,200
[45] Nov. 8, 1983

[54] POWDER STICK COMPOSITION FOR TOPICAL APPLICATION

[75] Inventors: John H. Murphy, Matamoras, Pa.; Jon D. Packer; Dennis R. Brown, both of Port Jervis, N.Y.

[73] Assignee: Kolmar Laboratories, Inc., Port Jervis, N.Y.

[21] Appl. No.: 130,969

[22] Filed: Mar. 17, 1980

[51] Int. Cl.³ .......................... A61K 7/02; A61K 7/34
[52] U.S. Cl. ................................ 424/63; 424/DIG. 5; 424/65; 424/66; 424/68
[58] Field of Search ................... 424/63, DIG. 5, 66, 424/68

[56] References Cited

U.S. PATENT DOCUMENTS

| 3,800,034 | 3/1974 | Kircher et al. | 424/63 |
| 3,846,556 | 11/1974 | Handjani et al. | 424/63 |
| 3,978,207 | 8/1976 | Fotin et al. | 424/63 |
| 4,119,712 | 10/1978 | Goldner et al. | 424/63 |

FOREIGN PATENT DOCUMENTS

| 968535 | 2/1958 | Fed. Rep. of Germany | 424/63 |
| 1492258 | 12/1969 | Fed. Rep. of Germany | 424/63 |
| 2365219 | 7/1974 | Fed. Rep. of Germany | 424/63 |
| 48-72341 | 9/1973 | Japan | 424/63 |
| 530682 | 4/1977 | U.S.S.R. | 424/81 |

OTHER PUBLICATIONS

Jenkins et al., The Art of Compounding, 1957, pp. 367 to 385, 396 to 402.

*Primary Examiner*—Dale R. Ore
*Attorney, Agent, or Firm*—Andrus, Sceales, Starke & Sawall

[57] ABSTRACT

A powder stick composition for topical application, and particularly a powder stick containing an anti-perspirant as an active ingredient. The stick is produced by incorporating an active ingredient, a finely divided inert filler, and a fatty alcohol with a siloxane at an elevated temperature to form a slurry. The slurry is then molded into stick form at atmospheric pressure, and the molded stick is dried to evaporate a major portion of the siloxane. The resulting stick is firm, has a uniform distribution of the active ingredient throughout the cross section and has excellent pay-off characteristics.

12 Claims, No Drawings

POWDER STICK COMPOSITION FOR TOPICAL APPLICATION

This is a continuation of application Ser. No. 945,241, filed Sept. 25, 1978 now abandoned.

BACKGROUND OF THE INVENTION

Antiperspirant products are frequently produced in stick form, such as wax sticks, soap gel sticks, and pressed powder sticks. A wax stick, in addition to the antiperspirant active ingredient, is composed of waxes and esters and contains a relatively high percentage of a solvent. Wax sticks have certain inherent disadvantages in that the waxes have a tendency to stain clothing, and the wax residue cannot be removed from the clothing by normal washing procedures. As the wax stick contains a high proportion of solvent, the solvent will evaporate if the stick is unsealed and exposed to the atmosphere, thereby resulting in shrinkage and "dog-boning" of the stick, with a resulting unattractive appearance.

As the wax stick has a relatively high proportion of solvent, this reduces the proportion of active ingredient that can be included in the stick, limiting the active ingredient to a maximum percentage of about 40%.

Soap gel anti-perspirant sticks have also been used in the past. The conventional soap gel system includes sodium stearate and a low molecular weight alcohol, such as ethanol, as well as an anti-perspirant active ingredient in a maximum amount of about 20%. In addition, soap gel sticks have normally used calcium carbonate as a filler. Because of the hygroscopic nature of the ingredients, the product has a tendency to absorb water, expand and crack. Furthermore, the calcium carbonate filler tends to neutralize the anti-perspirant, which is normally aluminum chlorohydrate, thereby rendering the anti-perspirant salt ineffective. As a further disadvantage, the alcohol will evaporate if the stick is exposed to the atmosphere, causing shrinking and "dog-boning" of the stick.

Attempts have also been made in the past to provide a dry, pressed powder, anti-perspirant stick. In sticks of this type, the active ingredient is incorporated with an inert filler and binder and the dry mixture is compressed or extruded at high pressure into stick form. The compression operation is slow and requires a dwell of several minutes at high pressure, making the process unsatisfactory from a commercial standpoint. Extrusion of the dry mixture is particularly difficult due to the abrasive nature of the dry powdered mixture. Further, in both compressing and extruding processes, the anti-perspirant active ingredient is damaging to the expensive processing equipment.

SUMMARY OF THE INVENTION

The invention is directed to a powder stick for topical application, such as an anti-perspirant stick, or a cosmetic stick, which is produced without the application of super-atmospheric pressures. In preparing the stick, the active ingredient, a fatty alcohol and a finely divided inert filler are mixed with liquid siloxane at an elevated temperature to form a slurry. The slurry is then molded into a stick form at atmospheric pressure, and after molding, the stick is dried in air to evaporate a major portion of the siloxane.

The resulting powder stick is hard and firm for stick strength, but yet will not glaze over during application to the skin.

As the dried stick has a relatively low residual proportion of the siloxane solvent, the stick is stable and will retain its shape and consistency, even if unsealed and exposed to the atmosphere for extended periods of time.

The liquid siloxane serves to disperse the fatty alcohol and results in a uniform distribution of the fatty alcohol throughout the filler, thereby providing uniform characteristics for the stick throughout its entire cross-section. The uniform distribution of the ingredients results in the stick being resistant to humidity absorption and prevents degradation of the stick under high humidity conditions.

As the siloxane is substantially entirely evaporated prior to packaging, the stick contains a high proportion of powder form ingredients, generally up to 90%.

Other objects and advantages will appear in the course of the following description.

DESCRIPTION OF THE PREFERRED EMBODIMENT

The powder stick of the invention is prepared from a slurry having the following general formulation in weight percent:

Finely divided inert filler: 70% to 10%;
Fatty alcohol: 5% to 30%;
Siloxane: 25% to 60%.

When preparing an anti-perspirant stick according to the invention, the slurry has the following formulation in weight percent:

Finely divided inert filler: 66% to 3%;
Anti-perspirant active ingredient: 10% to 35%;
Fatty alcohol: 4% to 12%;
Siloxane: 20% to 50%.

When preparing deodorant sticks according to the invention the slurry has the following formulation in weight percent:

Finely divided inert filler: 69.9% to 5%;
Fatty alcohol: 5% to 30%;
Deodorant active ingredient: 0.1% to 5%;
Siloxane: 25% to 60%.

In preparing a costmetic stick according to the invention, such as an eye shadow stick or blush stick, the slurry used in preparing the stick has the following formulation in weight percent:

Finely divided inert filler: 75% to 3%;
Fatty alcohol: 4% to 12%;
Cosmetic coloring materials: 1% to 35%;
Siloxane: 20% to 50%.

The finely divided filler can take the form of materials such as aluminum hydroxide, kaolin, talc, mica, corn starch, calcium carbonate, silicon dioxide, calcined clay, barium sulfate, aluminum oxide, aluminum silicate, and the like.

The fatty alcohols serve as a binder for the system and contain from 12 to 22 carbon atoms in the molecule. The fatty alcohol can take the form of cetyl alcohol, stearyl alcohol, and the like.

The siloxane is normally a liquid at room temperature. Chemically it is composed primarily of two components: $D_4$ cyclodimethicone and $D_5$ cyclodimethicone. The $D_4$ component represents the majority with the $D_5$ being a minor constituent. Chemically $D_4$ cyclodimethicone may be symbolically written as:

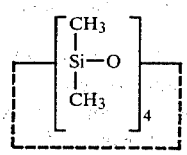

and D₅ cyclodimethicone may be symbolically written as:

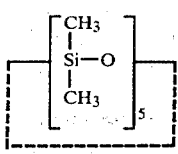

When preparing an anti-perspirant stick, the anti-perspirant active ingredient can be aluminum chlorohydrate, aluminum hydroxychloride, zirconium hydroxy chloride, aluminum chloride, or other acceptable anti-perspirant materials.

When forming a deodorant stick, the deodorant active ingredient can take the form of:
(A)—2,4,4'-trichloro-2'hydroxydiphenyl ether
(B)—1,-(2-hydroxyethyl) carbamoyl methyl pyridinium chloride laurate
(C)—Benzenthonium chloride
(D)—Zinc phenolsulfonate
(E)—Aluminum chlorohydroxide When preparing a cosmetic coloring stick, such as an eye shadow stick or blush stick, the cosmetically acceptable coloring materials can take the form of titanium dioxide, ferric ferrocyanide or ferric ammonium ferrrocyanide, iron oxides, ultramarines, chromium oxide, chromium hydroxide, pearlescents, organic dyes and lakes.

In addition to the above ingredients, the slurry can also contain small amounts, up to 2% by weight, of a fatty acid ester containing from 12 to 22 carbon atoms, such as iso-propyl myristate or isopropyl palmitate, which prevents dusting of the stick; and/or magnesium stearate which aid in preventing glazing of the stick; and/or a preservative such as methyl paraben or propyl paraben; or perfumes.

To prepare the powder stick of the invention, the fatty alcohol is dispersed in the liquid siloxane at a temperature of 60° C. to 70° C. The remaining ingredients, such as the filler, active ingredient and other additives, are then mixed into the liquid dispersion to provide a slurry. The slurry is then poured by gravity at atmospheric temperature into a case or mold. The slurry at this time has a temperature slightly above the solidification temperature of the siloxane-fatty alcohol slurry and generally in the range of about 50° C. to 60° C. On cooling, the slurry will solidify to form a solid stick.

The stick is then exposed to air movement, either by blowing air over the molded product or subjecting the molded product to a vacuum. In practice, the drying air preferably has a relative humidity of about 15% and is at a temperature in the range of about 25° C. to 30° C. The air movement serves to evaporate a major portion of the siloxane from the molded product so that the dried product has a residual siloxane content of less than 2% by weight. While it is possible to evaporate the entire siloxane content, it is normally uneconomical to go beyond the 2% level though this can be accomplished by variations in relative humidity and atmospheric pressure.

As the siloxane is a relatively expensive material, it is preferred to carry out the drying in a closed chamber or hood so that the siloxane vapor can be recovered for reuse through use of a condensing unit.

The resulting dried powder stick has excellent strength yet provides adequate pay-off on the skin and is not so hard that it will glaze over after several applications to the skin.

Through use of the siloxane solvent, the powdered ingredients and the fatty alcohols are uniformly distributed throughout the stick, thereby insuring the same level of effectiveness for each application to the skin.

As the dried product contains only a minimum proportion of the evaporable siloxane, and waxes and fatty esters, the product is stable even if exposed to the atmosphere, will remain effective over a substantial period of time and can be removed from fabric or clothing by machine washing with little or no stain effect.

The powdered stick of the invention is extremely resistant to humidity conditions and will not decompose or crumble under high humidity conditions.

As a further advantage, the product has a low level of dusting so as to be attractive to the consumer during use.

The following formulations in weight percent illustrate the preparation of the powder stick of the invention:

ANTI-PERSPIRANT STICK:
  Siloxane: 28.0;
  Aluminum Chlorohydrate: 18.0;
  Aluminum Hydroxide: 41.6;
  Stearyl Alcohol: 10.8;
  Isopropyl Myristate: 0.7;
  Magnesium Stearate: 0.7;
  Perfume: 0.2.
ANTI-PERSPIRANT STICK:
  Siloxane: 28.0;
  Aluminum Chlorohydrate: 28.8;
  Aluminum Hydroxide: 19.6;
  Kaolin: 10.0;
  Stearyl Alcohol: 10.8;
  Isopropyl Myristate: 0.7;
  Magnesium Silicate: 0.7;
  Spray Dried Fragrance: 1.4.
ANTI-PERSPIRANT STICK:
  Siloxane: 28.0;
  Aluminum Chlorohydrate: 28.8;
  Talc: 15.0;
  Cornstarch: 15.3;
  Cetyl Alcohol: 10.8;
  Isopropyl Palmitate: 0.7;
  Magnesium Stearate: 0.7;
  Perfume: 0.7.
ANTI-PERSPIRANT STICK:
  Siloxane: 28.0;
  Aluminum Chlorohydrate: 50.4;
  Kaolin: 8.9;
  Stearyl Alcohol: 10.8;
  Isopropyl Myristate: 0.7;
  Magnesium Stearate: 0.7;
  Perfume: 0.5.
EYE SHADOW STICK:
  Siloxane: 37.00;
  Stearyl Alcohol: 4.00;

Titanium Dioxide: 3.20;
Oxy Black 3068: 0.78;
Lo Micron Umber 2736: 6.45;
Aluminum Hydroxide: 38.07;
Methyl Paraben: 0.25;
Propyl Paraben: 0.10;
Germall 115: 0.15;
Flamenco Satina 100 Pearlescence: 7.00;
Flamenco Super Pearlescence: 3.00.

DEODORANT STICK:
Siloxane: 25.00;
Stearyl Alcohol: 10.00;
Calcium Carbonate: 53.25;
Cornstarch: 5.00;
Titanium Dioxide: 6.00;
Triclosan: 0.25;
Perfume: 0.50.

In all of the above samples, the fatty alcohol was added to the liquid siloxane at a temperature of 65° C. and the remaining ingredients were then blended into the liquid to form a slurry. In each case the slurry, at a temperature of about 55° C., was poured into plastic molds to form the sticks. Air at a temperature of 28° C. was passed over the sticks for a period of 72 hours to evaporate the major proportion of the siloxane to provide the finished stick composition. In each example the dried stick has a residual siloxane content of less than 2% by weight.

In molding the stick, the slurry can be poured directly into a component of the final package, or alternately, the slurry can be introduced into a separate mold and subsequently transferred to the package.

Various modes of carrying out the invention are contemplated as being within the scope of the following claims particularly pointing out and distinctly claiming the subject matter which is regarded as the invention.

We claim:

1. A method of preparing a cosmetic powder product, comprising the steps of mixing at an elevated temperature a fatty alcohol containing 12 to 22 carbon atoms in the molecule, a finely divided filler, and a sufficient quantity of a liquid cyclic evaporable siloxane to form a liquid moldable slurry, introducing the slurry into a mold, solidifying the slurry to provide a solid molded product, evaporating the major portion of the siloxane from the molded product to provide a dried powder product, and thereafter packaging said product, said product having excellent pay off and high resistance to humidity absorption.

2. The method of claim 1, wherein the slurry has the following composition in weight percent:
Fatty alcohol: 5% to 30%;
Filler: 70% to 10%;
Siloxane: 25% to 60%.

3. The method of claim 1, wherein the siloxane is at a temperature in the range of 60° C. to 70° C. during the step of mixing.

4. The method of claim 1, wherein the step of molding the slurry comprises pouring the slurry by gravity into a mold.

5. The method of claim 1, wherein said composition includes an active anti-perspirant ingredient, said slurry having the following composition in weight percent:
Fatty alcohol: 4% to 12%;
Anti-perspirant ingredient: 10% to 35%;
Filler: 66% to 3%;
Siloxane: 20% to 50%.

6. The method of claim 1, wherein said composition contains a cosmetic coloring material, said slurry having the following composition in weight percent:
Filler: 75% to 3%;
Fatty alcohol: 4% to 12%;
Cosmetic coloring material: 1% to 35%;
Siloxane: 20% to 50%.

7. The method of preparing a powdered anti-perspirant stick, comprising the steps of preparing a slurry composed of a finely divided generally inert filler, a fatty alcohol containing from 12 to 22 carbon atoms in the molecule, an anti-perspirant ingredient, and a liquid cyclic volatile siloxane; molding the slurry at atmospheric pressure into a stick, and evaporating the major portion of the siloxane from the stick to form a dried stick having a siloxane content less than 2% by weight, said slurry having the following composition in weight percent:
Fatty alcohol: 4% to 12%;
Anti-perspirant ingredient: 10% to 35%;
Filler: 66% to 3%;
Siloxane: 20% to 50%.

8. The method of claim 7, wherein the anti-perspirant material is aluminum chlorohydrate.

9. The method of claim 7, wherein the anti-perspirant material is zirconium hydroxy chloride.

10. The method of claim 7, wherein the step of evaporating the siloxane is carried out by flowing a gas over the molded stick.

11. A method of preparing a cosmetic powder product, comprising the steps of preparing a liquid slurry by mixing a finely divided filler, a fatty alcohol, and an evaporable solvent for the alcohol, said solvent being a liquid at room temperature, introducing the liquid slurry into a mold, solidifying the slurry to provide a solid molded product, evaporating the major portion of the solvent from the molded product to provide a dry powder product, and thereafter packaging the product, said product having excellent pay-off and high resistance to humidity absorption.

12. A powdered stick composition for topical application, consisting essentially by weight of from 95% to 5% of a finely divided inert filler, from 5% to 25% of a fatty alcohol containing 12 to 22 carbon atoms in the molecule, and up to 2% siloxane.

* * * * *